United States Patent [19]

Shaw et al.

[11] 4,331,491
[45] May 25, 1982

[54] METHOD OF MAKING PACKAGING USING A TINTED ADHESIVE LAMINATE

[75] Inventors: Peter M. Shaw, Whitehaven; Andrew F. Noble, Workington, both of England

[73] Assignee: Smith Brothers (Whitehaven) Limited, England

[21] Appl. No.: 146,718

[22] Filed: May 5, 1980

[30] Foreign Application Priority Data

Feb. 29, 1980 [GB] United Kingdom ............... 8006950

[51] Int. Cl.³ .................. B32B 31/08; B32B 31/20
[52] U.S. Cl. ......................... 156/64; 156/290; 156/324; 156/553; 156/555; 156/578; 427/8; 427/208.4; 428/200; 428/207; 428/212; 428/483; 428/511; 428/916
[58] Field of Search ................ 156/64, 220, 290, 291, 156/324, 547, 578, 553, 555; 427/8, 208.4; 428/207, 212, 318, 320, 321, 483, 511, 916, 200

[56] References Cited

U.S. PATENT DOCUMENTS

| | | | |
|---|---|---|---|
| 2,037,398 | 4/1936 | Smith | 428/202 |
| 2,084,081 | 6/1937 | Faber | 428/204 |
| 2,961,365 | 11/1960 | Sroog | 428/285 |
| 3,052,589 | 9/1962 | Ruscoe et al. | 156/277 |
| 3,219,506 | 11/1965 | Dusina et al. | 156/290 X |
| 3,684,641 | 8/1972 | Murphy | 156/291 X |
| 4,063,641 | 12/1977 | Kuehn et al. | 428/204 X |
| 4,223,058 | 9/1980 | Citron | 428/212 X |

FOREIGN PATENT DOCUMENTS

810513 4/1969 Canada ................ 156/290

*Primary Examiner*—Robert A. Dawson
*Attorney, Agent, or Firm*—William A. Drucker

[57] ABSTRACT

In a method of making packaging, especially for steam-sterilizable medical or pharmaceutical products, a tinted plastics sheet is formed as a laminate (34) comprising two substantially transparent sheets (10, 30) bonded together by a tinted adhesive (15). The sheet is then heat-sealed in selected areas (50, 52, 54) to a second sheet (40) to form a pouch (56) or tube to receive the product.

The arrangement ensures that one of the films will be between the adhesive and the product so that colorant cannot migrate and contaminate the product when subjected to high temperatures and vacuum during steam-sterilization.

The outer film may be polyester, the inner film a heat-sealable material such as cast polypropylene, and the second sheet may be paper.

9 Claims, 4 Drawing Figures

METHOD OF MAKING PACKAGING USING A TINTED ADHESIVE LAMINATE

The invention relates to a method of making packaging, especially for sterilized medical or pharmaceutical products suitable for various methods of sterilizing, such as steam, gas or irradiation and to the packaging itself.

Such products are often packaged in a pouch formed by sealing two superimposed sheets together at their margins by heat and/or pressure. Typically one sheet is of substantially transparent plastics material, permitting visual inspection of the product, and the other of paper or an alternative plastic which is sufficiently pervious to steam or gas to allow sterilization of the product after it has been sealed into the pouch. Both the paper and the plastics sheet are, of course, substantially impervious to bacteria.

It is desirable for the plastics sheet to be provided with a tint. Many users find a light-blue tint to be aesthetically pleasing and suggestive of cleanliness and even a superior product. It has also been suggested that if the sealable plastics sheet is lightly tinted the validity of the initial heat seal can be ascertained more readily by visual inspection since the sealed area is marked by a changed color intensity.

It is generally unsatisfactory, however, to tint the sealable plastic sheet of a package which is to be steam-sterilized in an autoclave since the colorant may migrate from the plastics sheet and contaminate the product.

An object of the present invention is to eliminate this problem and to this end in a method of making packaging for pharmaceutical or medicinal products a tinted plastics sheet is formed as a laminate by bonding together two substantially transparent plastics films by a tinted adhesive, preferably non-migrating and chemically cured. The laminated sheet so formed is then sealed in selected areas to a second sheet to form a container, for example a pouch or tube.

Thus, one of the plastics films separates the tinted adhesive from the interior of the package preventing contamination of the product by colorant even when subjected to the elevated temperatures (about 134° C.) and vacuum employed in a steam-sterilizing autoclave.

Preferably, after the laminate has been formed, but before sealing to the second sheet, the adhesive is allowed to cure chemically to optimize the bond strength. Quality control tests on the laminate may also be carried out at this stage in the process.

One of the films, that juxtaposed and sealed to the second sheet, may comprise heat-sealable material, for example cast polypropylene. The other film may comprise polyester or other suitable plastic. The second sheet may be paper or alternative plastics.

Advantageously the adhesive is applied to one of the films by a roller, application of the adhesive then being monitored by observing the adhesive coating on the roller, and transferred to the film from the roller.

Specific implementation of the invention will now be described by way of example only and with reference to the accompanying drawing, in which.

Figure 1:
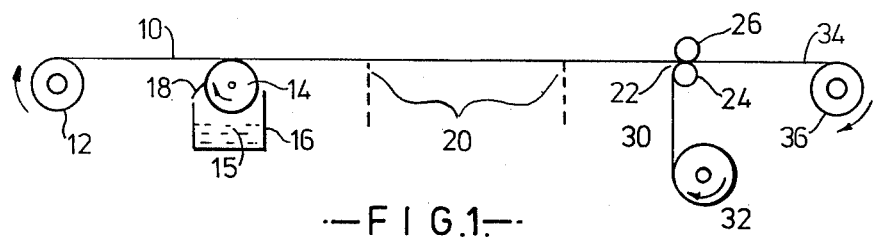
FIG. 1 illustrates, schematically, formation of a tinted laminated plastics sheet.

Referring to FIG. 1, a web 10 of substantially transparent polyester or alternative plastic film is fed from a reel 12, rotating clockwise as shown, to pass in contact with the circumferential surface of a roller 14, also rotating clockwise. As it rotates, the surface of the roller 14 receives a coating of adhesive 15 from a tank 16, located beneath the roller, and transfers it to the film 10. The adhesive, which is tinted light-blue, is received in minute indentations covering the entire circumferential surface of the roller 14 (formed by chemical or mechanical etching process). Excess adhesive may be removed by a doctor blade 18 in wiping contact with the roller at a position between the tank 16 and the film 10.

The adhesive-coated web 10 then passes through a drying zone 20, of any suitable known type, where solvent is removed from the adhesive. Thereafter the web 10 passes through a nip 22 between two pressure rollers 24, 26, which may or may not be heated.

A web of substantially transparent cast polypropylene film 30, of a similar width as the polyester web 10, from a reel 32, also passes through the nip 22 in contact with the adhesive-coated surface of the web 10. Under the action of the heat and/or pressure applied by the rollers 24 and 26, the two webs 10 and 30 are bonded together across their entire width and emerge as a light-blue tinted laminated sheet 34 which is then wound onto a reel 36. The reel of tinted laminated sheet is stored for a minimum period of 72 hours to allow the adhesive to cure chemically.

Figure 2:
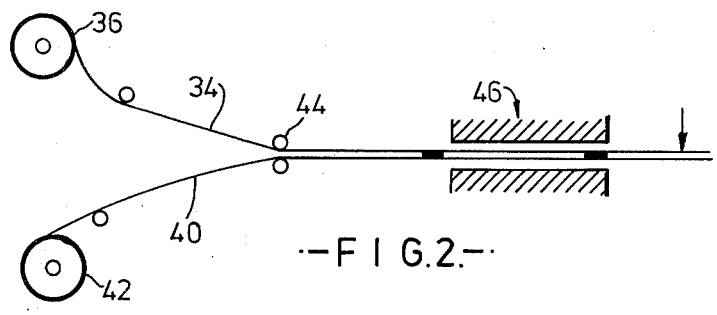
FIG. 2 illustrates subsequent sealing of the sheet to a paper web to form discrete packages.

When the adhesive has cured, the laminated sheet 34 is slit to desired width and sealed to a sheet 40 of machine-glazed bleached kraft paper. As illustrated in FIG. 2, the tinted plastics sheet 34 and the paper sheet 40 are unwound from their respective reels 36 and 42 and brought together between a pair of guide rollers 44.

Figure 3:
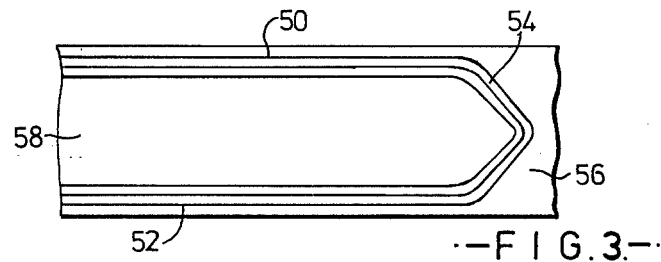
FIG. 3 is a plan view of such a package.

Heat and pressure are applied, in known manner, as at 46, to seal the two sheets together along their edges as at 50, 52, and, at one position, across their width as at 54. The sheets are then cut transversely by a knife 48 to form pouches 56, as shown in FIG. 3, having one end 58 open to receive the product. The end 58 of the pouch will then also be heat-sealed and the sealed pouch and its contents sterilized in a steam autoclave, usually at about 134° C., or in accordance with one of several accepted practices. Alternatively the two sheets may simply be sealed at 50 and 52 to form a length of tubing which is wound into a reel form for supply to user.

Figure 4:
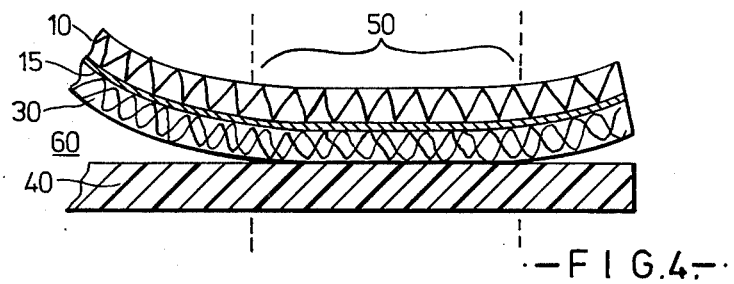
FIG. 4 shows a section through the heat-sealed part of the package.

FIG. 4 shows a section through the sealed part of the pouch, from which it can be seen that the adhesive layer 15 is isolated from the interior 60 of the pouch 50 by the polypropylene film 30. This segregation ensures that the light-blue colourant cannot migrate from the adhesive and contaminate the contents of the package. It should also be noted that chemical curing of the adhesive will also tend to inhibit colorant migration during steam sterilization.

In addition to overcoming the problem of contamination of the product, incorporating the tint into the adhesive also aids control of the quality of the laminated sheet itself. It is important that the adhesive be applied to the polyester film 10 in a continuous layer of optimum thickness without imperfections. Too thin a coating of adhesive will result in poor adhesion. If localized areas are not coated at all, a corresponding blemish or bubble may result which is unsightly and may result in a functional fault in the final package.

That the correct amount of adhesive is being applied is checked conveniently by visually inspecting the adhesive-coated roller 14, and it is found that accurate assessment of continuity and uniformity of the coating is easier when the adhesive is tinted rather than clear.

A further advantage obtained by tinting the adhesive is that visual inspection of the laminated plastic sheet for bubbles or other imperfections is easier and the choice of light-blue has been found to reduce eye-strain and fatigue in the inspection.

As mentioned in the introduction, it has been suggested previously that the validity of the initial heat seal can be ascertained more readily if one of the sheets if lightly tinted, due to a change in color intensity at the seal. This approach has been found unsatisfactory since the colour intensity change can be produced merely by contact without significant adhesion, especially if the surfaces to be heat-sealed together are contaminated, for example by grease. Accordingly, while the invention could be employed in the manufacture of such products, it is preferable, even essential, at least for food, medicinal or pharmaceutical products, to assure seal integrity by physical testing of samples, for example as laid down by the United Kingdom Dept. of Health and Social Security Specification TSS/S/330,010 for "Heat Sealable Pouches and Tube Material converted from Plastics Film and Paper for containing steam sterilised Medical Items", which requires minimum seals strengths of 150 g/15 mm and assurance that the materials and seals will withstand high vacuum autoclaving.

We claim:

1. A method of making packaging for medical or pharmaceutical products, including forming a tinted laminated plastics sheet by bonding together two substantially transparent plastics films and sealing the sheet in selected areas to a second sheet to form a container for the product, wherein the films are bonded together by a tinted adhesive.

2. A method as claimed in claim 1, wherein the adhesive is at least partially dried before the films are superimposed to form the laminate.

3. A method as claimed in claim 1 or 2, wherein the laminate is stored for a predetermined period to allow the adhesive to cure chemically before sealing to the second sheet.

4. A method as claimed in claim 1, wherein the laminate is inspected for uniformity of adhesion, clarity and/or bond strength before said sealing to the second sheet.

5. A method as claimed in claim 1, wherein one of the films comprises a heat-sealable plastics material, that film being sealed to the second sheet in said selected areas.

6. A method as claimed in claim 1 wherein the second sheet comprises paper.

7. A method as claimed in claim 1, wherein the plastics films comprise continuous webs.

8. A method as claimed in claim 1, including the step of applying the tinted adhesive to one or both films by means of a roller.

9. A method as claimed in claim 8, including the step of visually monitoring the tinted adhesive coated roller.

* * * * *